Figure 1:
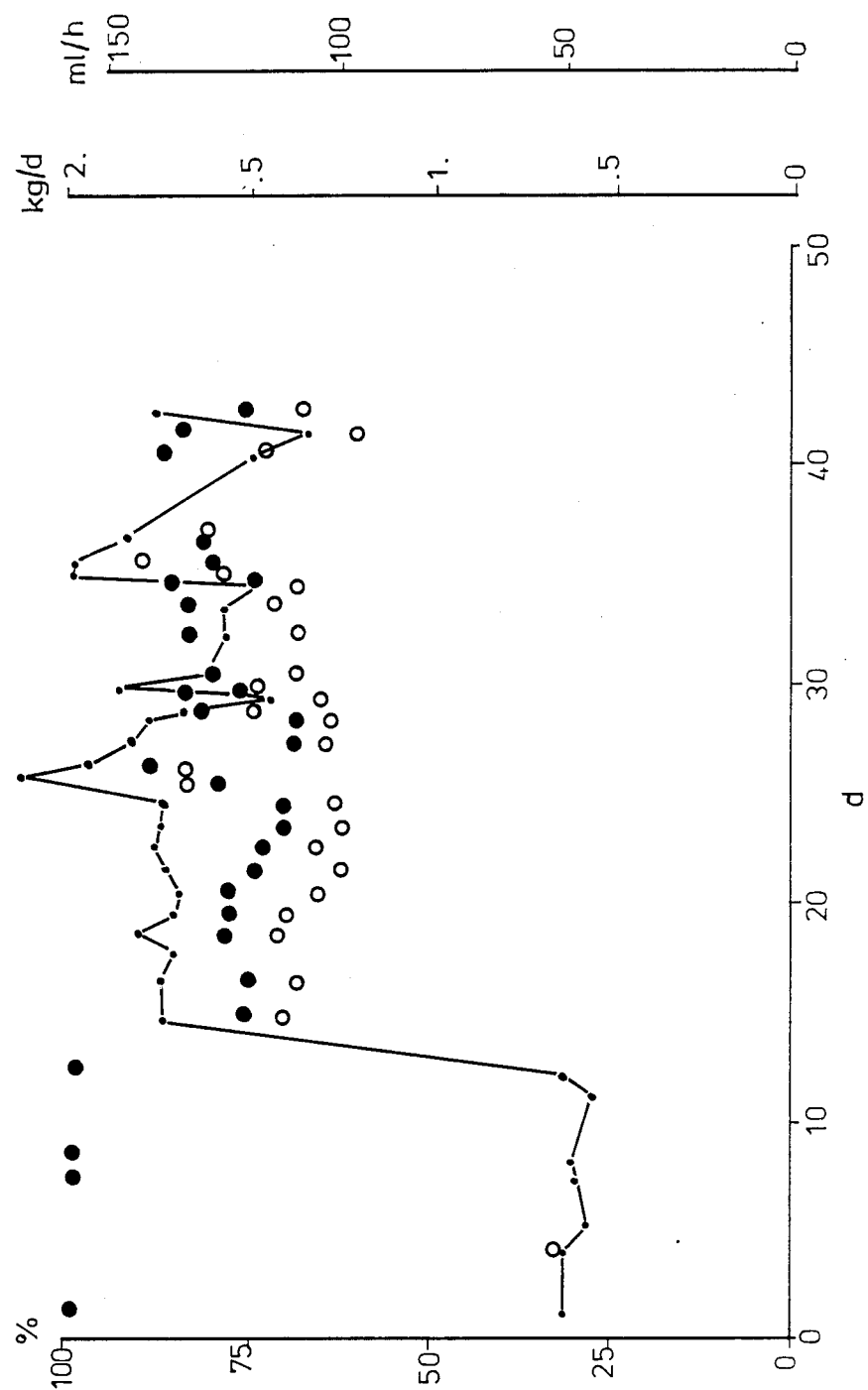
Figure 2:
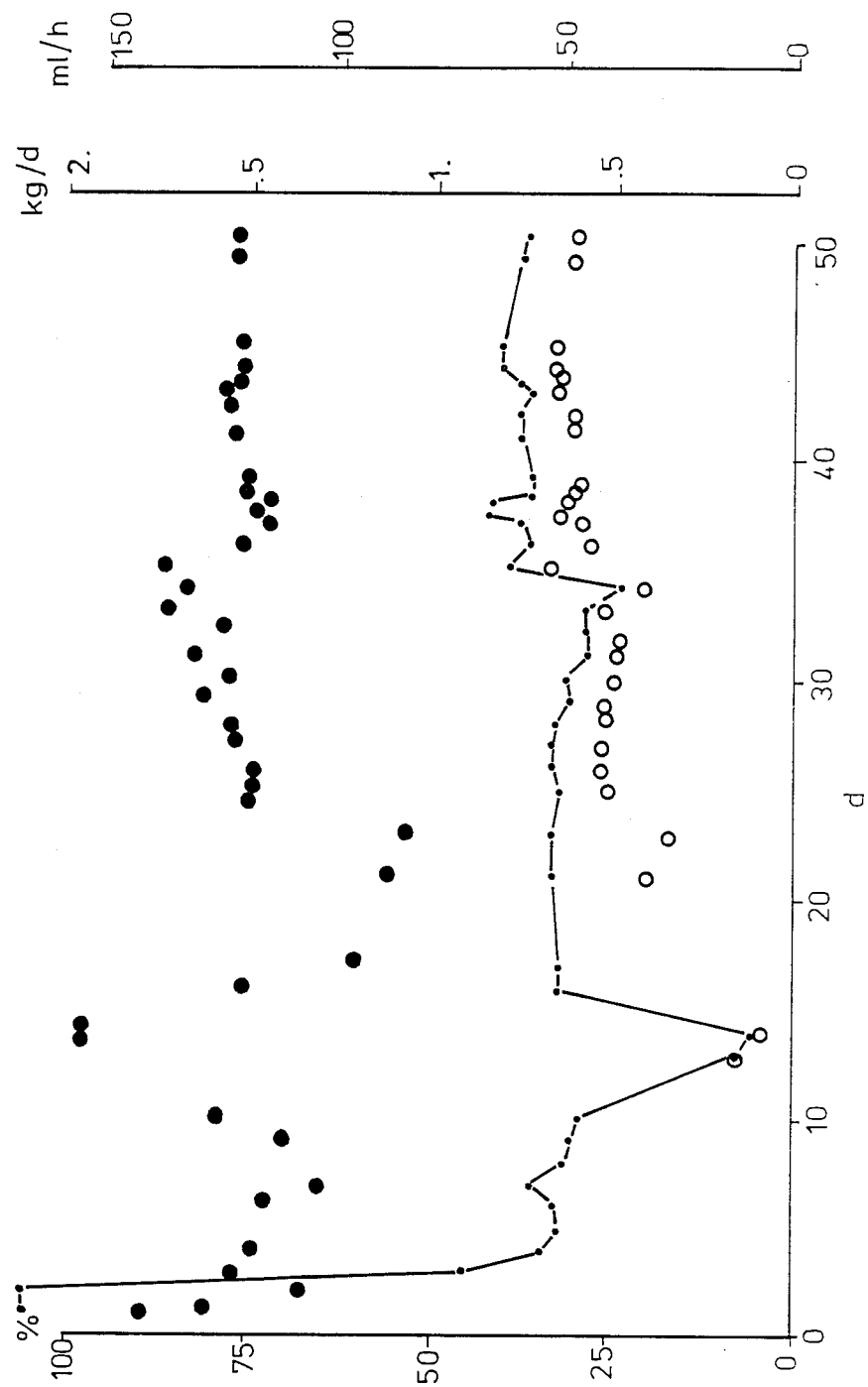

United States Patent [19]

Egerer et al.

[11] Patent Number: 4,774,178

[45] Date of Patent: Sep. 27, 1988

[54] IMMOBILIZATION OF BIOLOGICAL MATERIAL WITHIN A POLYMER MATRIX

[75] Inventors: Peter Egerer, Wuppertal; Wilfried Haese, Mönchengladbach-Neuwerk; Hermann Perrey, Krefeld; Günter Schmidt-Kastner, Wuppertal-Elberfeld, all of Fed. Rep. of Germany

[73] Assignee: Bayer Aktiengesellschaft, Leverkusen, Fed. Rep. of Germany

[21] Appl. No.: 727,693

[22] Filed: Apr. 26, 1985

[30] Foreign Application Priority Data

May 2, 1984 [DE] Fed. Rep. of Germany ....... 3416141
May 2, 1984 [DE] Fed. Rep. of Germany ....... 3416142
Jul. 28, 1984 [DE] Fed. Rep. of Germany ....... 3427888
Jul. 28, 1984 [DE] Fed. Rep. of Germany ....... 3427890

[51] Int. Cl.$^4$ .................. C12P 1/00; C12N 11/08; C12N 11/04; C07K 17/08
[52] U.S. Cl. ..................... 435/41; 435/180; 435/182; 530/817
[58] Field of Search ............ 435/41, 100, 174, 180, 435/181, 182; 530/817

[56] References Cited

U.S. PATENT DOCUMENTS

| | | | |
|---|---|---|---|
| 3,791,927 | 2/1974 | Forgione et al. | 435/182 |
| 3,859,169 | 1/1975 | O'Driscoll et al. | 435/182 |
| 3,860,490 | 1/1975 | Guttag | 435/182 |
| 4,195,129 | 3/1980 | Fukui et al. | 435/182 |
| 4,342,834 | 8/1982 | Wood et al. | 435/182 |
| 4,390,627 | 6/1983 | Iantero, Jr. | 435/180 |
| 4,582,805 | 4/1986 | Bozzelli et al. | 435/180 |

*Primary Examiner*—David M. Naff
*Attorney, Agent, or Firm*—Sprung Horn Kramer & Woods

[57] ABSTRACT

Biological material such as microorganisms is immobilized by polymerizing in the presence of the biological material a readily soluble polyetherpolyol having some hydroxyl groups esterified with acrylic and/or methacrylic acid and remaining hydroxyl groups reacted with an isocyanate group-containing derivative of an unsaturated carboxylic acid or a polyfunctional isocyanate. Preferably, the isocyanate derivative of an unsaturated carboxylic acid is isocyanatoethyl acrylate, isocyanatoethyl methacrylate of 4-isocyanato-3-methyl-2-butyl-acrylate and the polyfunctional isocyanate is a diisocyanate or polyisocyanate. Beads can be produced by forming droplets in a water-immiscible medium and polymerizing. Polymerization can be carried out under inert gas in the presence of radical initiators or by irradiation with actinic light.

19 Claims, 2 Drawing Sheets

IMMOBILIZATION OF BIOLOGICAL MATERIAL WITHIN A POLYMER MATRIX

The invention relates to a process for the immobilization of biological material by inclusion in polymerized compounds, where appropriate in the form of beads, to the immobilized biological material obtainable by this process, and to its use for biotransformations.

As a rule, the immobilization of biocatalysts leads to advantages in processing technology and economics. It is possible by the immobilization to modify chemical and physical properties, and sometimes also the selectivity and specificity of the biocatalyst.

In general, the methods for immobilization may be divided into the following groups
  adsorption onto finished carriers
  covalent bonding to carriers
  crosslinking
  inclusion in a polymer matrix.

The inclusion process is based on the biomaterial undergoing, in respect of its range of movement, inclusion during polymerization in a lattice of more or less uniform mesh and pore size. It should be impossible for the biocatalyst to pass through this polymer lattice, while it should offer virtually no resistance to the substrate and the product of a reaction carried out on this catalyst.

Conventional processes use low molecular weight, hydrophilic monomers to construct the lattice, for example hydroxyethyl acrylate, hydroxyethyl methacrylate, hydroxypropyl acrylate, hydroxypropyl methacrylate, acrylamide and others, which are mixed with the aqueous solution or dispersion of the biomaterial and are then polymerized.

For example, in U.S. Pat. No. 3,788,950, monofunctional acrylic acid derivatives, such as acrylamide, are used with a small amount of crosslink, such as N,N-methylenebisacrylamide. In U.S. Pat. No. 3,859,169, for example monoesters of acrylic acid with glycols are used in conjunction wIth a crosslinker and a soluble polymer. U.S. Pat. No. 3,860,490 describes the use of low molecular weight hydroxyalkyl acrylates and methacrylates for the formation of the polymer lattice.

However, in almost all processes difficulties arise in the control and reproducibility of the permeabilities for the biological material and for its substrates and products. However, these parameters are essential for suitability as an immobilizing material. In addition, the use of low molecular weight acrylic acid derivatives is disadvantageous because of their toxicity. It is possible for damage to the biocatalyst to occur during polymerization, or residual monomers present in the polymer greatly limit the use of the immobilized biocatalyst for the preparation of products for the foodstuffs industry or for the pharmaceutical industry.

In almost all these processes, however, materials such as films, foils, cast articles and others can be obtained only by external molding. In order to use these materials, it is frequently necessary to carry out subsequent processing, but it is hardly possible to attain by this the spherical shape which is favorable for catalysts.

U.S. Pat. No. 3,860,490 mentions the possibility of preparing beads by suspension polymerization in an inert medium but, due to the use of low molecular weight hydroxyalkyl acrylates and methacrylates, the same disadvantages and difficulties as have been mentioned above exist with this process.

A process for the immobilization of biological material by inclusion in polymerizable compounds has now been found, which process essentially comprises the use as the polymerizable material of high molecular weight polymerizable compounds which are readily soluble in water, contain two or more polymerizable functional group per molecule and have a molecular weight of over 400.

Accordingly, the invention relates to a process for the immobilization of biological materal by inclusion in polymerizable compounds, which is characterized in that aqueous solutions or dispersions of the biological material are mixed with an aqueous solution of high molecular weight polymerizable compounds which are readily soluble in water, contain two or more polymerizable functional groups per molecule and have a molecular weight of over 400, and the mixture is polymerized.

It is possible, due to the use of the high molecular weight water-soluble compounds which are used according to the invention and preferably contain two or more unsaturated groups and are curable, to achieve improved control and reproducibility of the permeabilities, since these properties are essentially determined by the high molecular weight water-soluble compounds. In addition, due to the use of, in particular, high molecular weight compounds, there are no toxicity problems. Moreover, low molecular weight toxic contaminants can be removed before the mixing with the biological material.

Furthermore, it has been found that the compounds according to the invention, which are readily soluble in water, can first be dissolved in a particular amount of water, buffer solution, salt solution and the like, by which means this polymer solution can be suited to the aqueous solution or dispersion of the biological material in respect of certain properties such as pH, salt concentration, viscosity and others. Subsequently, the two solutions or the aqueous polymer solution and the cell dispersion are mixed and polymerized. This process has particular advantages for sensitive biocatalysts which are not exposed to any abrupt changes 1n the surrounding medium during polymerization, by which means a loss of activity in the preparation of the polymerisable mixture is essentially avoided.

Another advantage of the present invention is the great absorptive capacity of the polymer for aqueous solutions and suspensions, which is associated with the ready solubility in water. Ratios of weight of aqueous biological material to the polymer between 1:1 and 30:1 are possible, and ratios between 4:1 and 20:1 are particularly suitable.

Since it is possible for the water content of the immobilized biological material to be large before and after the polymerization, the biomaterials exist in a particularly suitable, non-injurious environment, by which means the activity can be maintained stable and by which means, in addition, the flow of substrate and product are favored. The properties of the polymer lattice can be varied to a great extent by variation in the structure and molecular weight of the high molecular weight polymerizable compounds which are readily soluble in water. It is possible by this means to optimize the density of crosslinking, the permeability, the swelling behavior and other properties, in order to meet the requirements of the biological material.

The immobilized biomaterial can acquire virtually any desired shape during polymerisation by molding. It is possible to produce foils, films, molded articles, etc.

Furthermore, the mechanical properties can be modified by incorporation of strengthening fabrics. It is likewise possible to coat electrodes, membranes or other materials.

Furthermore, a process for the preparation of immobilized biological material by inclusion in polymerized compounds has been found, which is characterized in that an aqueous solution or dispersion of a biological material is mixed with an aqueous solution of high molecular weight polymerizable compounds which are readily soluble in water, contain two or more polymerizable functional groups per molecule and have a molecular weight of over 400, and this mixture is dispersed as beads in an inert liquid medium and polymerized. It is possible to use as the interphase in particular substances which are immiscible with water, such as, for example, aliphatic, cycloaliphatic and aromatic hydrocarbons, such as, for example, hexane, cyclohexane and toluene, as well as halogenated derivatives of these, furthermore alcohols, ethers, esters or other substances which are immiscible with water, as well as silicone oils and paraffin oils, or mixtures of these with one another.

The preparation, which is possible by this process, of biocatalysts in the form of beads has particular advantages on use of the immobilized biomaterial. On the one hand, the spherical shape is particularly suitable for packing column reactors, and good flow is ensured, it is possible to avoid stoppages and, at the same time, the large surface area results in a good reaction rate for the reaction on the biocatalyst. Because of the hydrodynamic properties, the spherical shape is also particularly suitable in flow systems.

Furthermore, the present process represents a simplification and improvement of the previous processes. The spherical shape is obtained immediately during polymerization and can be readily controlled by the process conditions.

For example, the polymerization can be carried out in the form of a dispersion of the, as yet unpolymerized, biological material in an inert liquid medium such as, for example, aliphatic, cycloaliphatic and aromatic hydrocarbons, or functional derivatives of them, or silicone oils and paraffin oils, it being possible to vary widely the size of the beads which depends on the distribution, which can be achieved by stirring, passing in inert gas, for example nitrogen, or other metering in of the aqueous phase, for example by pumping or spraying into the inert phase. Furthermore, the viscosity, density, surface tension etc. of the aqueous or inert phase, which likewise affects the diameter of the beads, can be altered by additives.

Mean diameters of the beads of 0.05 mm to 5 mm are possible in this way, beads of larger diameter, for example greater than 2 mm, setting up a high diffusion resistance to the desired reaction. Particularly advantageous are beads having a mean diameter of 0.2 mm to 2 mm.

In addition to the simplicity of the preparation of the beads, there are advantages for the immobilization in respect of manipulation of the biomaterial under sterile conditions, since the process from the mixing to the finished immobilized material can be carried out in a closed system. The immobilized biomaterial can then easily be obtained by filtration. However, it is also possible to cool the entire mixture to below 0° C. in order thus to be able to store the material for a prolonged period. The cooling can also be extended beyond the solidification point of the external medium, it also being possible to lower this solidification point by additives or admixtures of other substances.

The invention also relates to a process for the preparation of immobilized biological material by inclusion in polymerized compounds, which is characterized in that an aqueous phase which contains both the biological material and the high molecular weight polymerizable compounds is dispersed in a second, non-aqueous, inert phase to produce beads, and this aqueous phase in the form of beads is polymerized.

A process of this type for the preparation of immobilized biological material by inclusion in polymerized compounds is characterized in that an aqueous solution or dispersion of a biological material is mixed with an aqueous solution of high molecular weight polymerizable compounds which are readily soluble in water, contain two or more polymerizable functional groups per molecule and have a molecular weight of over 400, and this mixture is dispersed in an inert liquid medium to produce beads, and is polymerized.

It is possible to use as the inert medium in particular substances which are immiscible with water, such as aliphatic, cycloaliphatic and aromatic hydrocarbons and derivatives of them, silicone oils, paraffin oils or mixtures of them with one another.

The ratio of the weight of the aqueous phase to the inert phase should be between 1:1 and 1:20.

The dispersion of the aqueous phase to produce beads can be brought about by stirring and/or passing through inert gas or by spraying the aqueous phase into the inert phase.

The polymerization by irradiation with actinic light can be carried out with the addition of photosensitizers which are poorly soluble or insoluble in the inert phase.

The compounds used for the immobilization are soluble in water, of high molecular weight, polymerizable, contain two or more polymerizable functional groups per molecule and have a molecular weight of over 400, in particular between 1,000 and 10,000, in particular compounds having ethylenically unsaturated groups.

In respect of their structure, they can be described as compounds which are produced in the reaction of high molecular weight hydrophilic compounds with compounds which contain polymerizable ethylenically unsaturated groups. Both participants in this reaction must contain functional groups which permit them to be chemically linked with one another or themselves, or linked with one another or themselves with the aid of difunctional or polyfunctional reagents.

Examples of high molecular weight hydrophilic compounds of this type are polyethylene glycols, ethylene oxides/propylene oxide block polymers and copolymers, alkoxylated, in particular ethoxylated, dihydric or polyhydric alcohols, and polymers which are readily soluble in water, for example wholly or partially hydrolyzed polyvinyl acetates, polycondensates which are readily soluble in water, such as, for example, polyesters prepared from the abovementioned high molecular weight hydrophilic compounds with dicarboxylic or polycarboxylic acids and polyaddition compounds which are readily soluble in water, such as, for example, polyether-polyurethanes prepared from the abovementioned high molecular weight hydrophilic compounds with diisocyanates or polyisocyanates.

Furthermore, the hydroxyl groups contained in the abovementioned high molecular weight hydrophilic compounds can be wholly or partially converted into amino groups by customary processes, such as, for example, reaction with ammonia.

The following are examples of suitable compounds having polymerizable ethylenically unsaturated groups: unsaturated carboxylic acids, acid chlorides, dicarboxylic acids, acid anhydrides or their functional derivatives.

The following are preferred: acrylic acid, methacrylic acid, crotonic acid, acryloyl chloride, methacryloyl chloride, itaconic acid, fumaric acid, maleic acid, maleic anhydride, itaconic anhydride, glycidyl acrylate, glycidyl methacrylate, hydroxyethyl acrylate, hydroxypropyl acrylate, hydroxyethyl methacrylate, hydroxypropyl methacrylate, isocyanatoethyl acrylate, isocyanatoethyl methacrylate and 4-isocyanato-3-methyl-2-butyl acrylate.

Thus the nature of the linkage of the high molecular weight hydrophilic compounds with the polymerizable ethylenically unsaturated compounds varies very widely, for example ester, ether, urethane, amide, amine and urea bonds are formed. The production of this linkage can be carried out by processes known from the literature, that is to say for example by reaction of the hydroxyl or amino groups with acids, acid halides or acid anhydrides to give the corresponding esters or amides, with epoxides to give the corresponding ethers or amines, or with isocyanates to give the corresponding urethanes or ureas.

Furthermore, in addition to the direct lnkage of the high molecular weight hydrophilic compounds with the compounds which contain the ethylenically unsaturated groups, the linkage can also be brought about by means of bifunctional or polyfunctional reagents.

Examples of bifunctional or polyfunctional reagents of this type are difunctional or polyfunctional isocyanates such as isophorone diisocyanate, toluylene diisocyanate, hexamethylene diisocyanate, polyisocyanates containing biuret groups (for example Desmodur N, product of the reaction of hexamethylene diisocyanate with water), polyisocyanates which are produced in the reaction of diisocyanates with polyhydric alcohols (for example Desmodur L, product of the reaction of toluylene diisocyanate with trimethylolpropane) and diepoxides or polyepoxides such as, for example, bisphenol A diglycidyl ether or diglycidyl hexahydrophthalate. The linkage of these reagents takes place, for example, with the hydroxyl groups of the high molecular weight hydrophilic compound and the compounds which contain hydroxyl groups and contain polymerizable ethylenically unsaturated groups, with the formation of urethanes or ethers.

It is also possible for the preparation of the compounds according to the invention to combine together the various modes of linkage.

However, the nature and proportion of the high molecular weight hydrophilic compounds, of the compounds which carry the ethylenically unsaturated groups and, where appropriate, of the difunctional or polyfunctional reagents must be selected so that the high molecular weight polymerizable compounds which are prepared from them according to the invention are so hydrophilic that the ready solubility in water and the large absorptive capacity for aqueous solutions or dispersions of biological material are present.

The following may be mentioned as preferred high molecular weight polymerizable compounds which are soluble in water:

Compounds which have been prepared from polyether-polyols, some of whose hydroxyl groups have been esterified with unsaturated carboxylic acids and the remainder have been reacted with derivatives, which contain isocyanate groups, of unsaturated carboxylic acids.

The following may be mentioned as particularly preferred:

Compounds which have been prepared from polyethylene glycols having a molecular weight above 400, some of whose hydroxyl groups have been esterified with acrylic acid or methacrylic acid and the remainder have been reacted with isocyanatoethyl acrylate and/or isocyanatoethyl methacrylate and/or 4-isocyanato-3-methyl-2-butyl-acrylate.

In the preparation, it is possible for some of the hydroxyl groups in the polyether-polyols first to be reacted with the derivatives, which contain isocyanate groups, of unsaturated carboxylic acids and then the remainder to be esterified with the unsaturated carboxylic acids, but it is preferable first to react some with the unsaturated carboxylic acids and then to react the remainder of the hydroxyl groups with the derivatives, which contain isocyanate groups, of unsaturated carboxylic acids. Thus the invention relates to a process which is characterized in that the high molecular weight polymerizable compounds which are readily soluble in water have been prepared from polyether-polyols, some of whose hydroxyl groups have been esterified with unsaturated carboxylic acids and the remainder have been reacted with derivatives, which contain isocyanate groups, of unsaturated carboxylic acids.

The process is characterized in that (a) the polyether-polyols are polyethylene glycols having a molecular weight of 400 and above, (b) the unsaturated carboxylic acid is acrylic acid and/or methacrylic acid, and (c) the isocyanate group-containing derivative comprises at least one member selected from the group consisting of isocyanatoethyl acrylate and/or isocyanatoethyl methacrylate and/or 4-isocyanato-3-methyl-2-butyl acrylate.

Furthermore, the following may be mentioned as preferred high molecular weight polymerizable compounds which are soluble in water:

Compounds which have been prepared from polyether-polyols, some of whose hydroxyl groups have been esterified with unsaturated carboxylic acids and the remainder have been reacted with difunctional or polyfunctional isocyanates.

In this context, the following may be mentioned as particularly preferred:

Compounds which have been prepared from polyethylene glycols having a molecular weight greater than 400, some of whose hydroxyl groups have been esterified with acrylic acid or methacrylic acid and the remainder have been reacted with isophorone diisocyanate, toluylene diisocyanate, polyisocyanates containing biuret groups or polyisocyanates which have been produced from the reaction of diisocyanates with polyhydric alcohols.

In the preparation, it is possible for some of the hydroxyl groups of the polyether-polyols first to be reacted with the difunctional or polyfunctional isocyanates and the remainder then to be esterified with unsaturated carboxylic acids. However, it is more advantageous first to carry out the partial esterification and then to carry out the reaction with the difunctional or polyfunctional isocyanates.

Thus the invention relates to a process which is characterized in that the high molecular weight polymerizable compounds which are readily soluble in water have been prepared from polyether-polyols, some of whose hydroxyl groups have been esterified with unsaturated carboxylic acids and the remainder have been reacted with difunctional or polyfunctional isocyanates.

The process is characterized in that (a) the polyether-polyols are polyethylene glycols having a molecular weight of 400 and above, (b) the unsaturated carboxylic acid is acrylic acid and/or methacrylic acid, and (c) the at least difunctional isocyanate comprises at least one member selected from the group consisting of isophorone diisocyanate, toluylene diisocyanate, hexamethylene diisocyanate, polyisocyanate containing biuret groups and a polyisocyanate which has been produced from the reaction of a diisocyanate with a polyhydric alcohol.

The polymerization can be carried out under inert gas and in the presence of customary radical initiators such as azobis(isobutyronitrile), t-butyl peroctoate, benzoyl peroxide, dicyclohexyl peroxydicarbonate, methyl ethyl ketone peroxide, cumene hydroperoxide, acetyl cyclohexanesulphonyl peroxide, dicumyl peroxide, potassium peroxidisulphate or ammonium peroxidisulphate, and can take place by redox systems such as potassium peroxidisulphate/riboflavin, potassium peroxidisulphate/sodium bisulphite, or hydrogen peroxide/compounds of divalent iron. It is likewise possible for a large number of compounds to act as accelerators, for example N,N,N',N'-tetramethylethylenediamine or β-dimethylaminopropionitrile.

Another option for the polymerization comprises irradiation of the mixture with actinic light. Suitable for this purpose are, for example, high pressure mercury lamps, low pressure mercury lamps, fluorescent lamps, xenon lamps, carbon arcs and solar radiation. Irradiation with electron beams or gamma rays is likewise possible, but a certain degree of damage to the biological material must be expected. It is also possible to accelerate the photopolymerization by photosensitizers. It is possible to use known photosensitizers such as α-carbonyl alcohols, for example benzoin or acetoin, aclyoin ethers such as benzoin methyl ether, benzoin ethyl ether and benzoin isopropyl ether, α-substituted acyloins such as α-methylbenzoin and α-methoxybenzoin and others, and derivatives which have been modified, and thus made soluble in water, by ionic groups such as, for example, carboxylic acid, sulphonic acid or amino groups.

In addition, it is possible to use polycyclic aromatic compounds such as naphthol and hydroxyanthracene, azo-amides such as, for example, 2-cyano-2-butylazoformamide, and metal salts, such as uranyl nitrate and iron chloride, as well as mercaptans, disulphides, halides and dyestuffs.

Advantages in respect of the economic efficiency of the process also result from the high absorptive capacity for water—particularly suitable ratios of the weight of the aqueous solution of suspension of the biological material to that of the polymer are between 4:1 and 20:1—which the immobilized material has before and after the polymerization. By this means it is possible, on the one hand, for inclusion of large amounts of aqueous solutions or dispersions of the biological material in a relatively small amount of the polymerizable compounds to be brought about and, on the other hand, it is possible by this means to immobilize fermentation broths immediately or following concentration, for example by microfiltration or centrifugation.

In addition however, it is also possible before and after the immobilization to use smaller amounts of water or aqueous solutions, and to replace part of the proportion of water by other liquids such as, for example, alcohols.

It is also possible to employ the immobilized biological materials in other than aqueous solutions, for example in aliphatic or aromatic hydrocarbons. Furthermore, it is possible to dry the polymerized material containing the biological material, especially in the case of beads. Thus the immobilized biological material can be stored over a long time and can be reused after rehydration. In order to retain most of the biological activity of the material, especially its catalytic activity, the drying can be done by passing warm, dehydrated air over the polymerized product by vacuum drying or under similarly mild conditions.

The processes described are characterized in that cells or enzymes are immobilized in the presence of disinfectants, bactericides or fungicides, are thus chemically sterilized and are transferred into the bioreactor, and the sterilizing agents are washed out of the closed, sterile reactor system before the reaction is started.

The biological materials, in particular cells or enzymes, which have been immobilized by the above process can be used as biocatalysts for biotransformations.

The following are microorganisms which are of interest for the immobilization according to the invention: Aspergillus niger, Gluconobacter suboxydans, Gluconobacter oxydans, Escherichia coli, Saccharomyces cerevisiae, Protaminobacter rubrum, Serratia plymuthica, Pseudomonas putida, Cunninghamella elegans, Clostridia such as, for example, *Clostridium thermoaceticum, Clostridium kluyveri, Clostridium butyricum, Clostridium sporogenes, Bacillus licheniformis, Streptomyces olivaceus.* Examples Example 1

Immobilization of alcohol dehydrogenase 48.7 g of polyethylene glycol with a mean molecular weight of 800 (produced by Chemische Werke Hüls) were esterified with 4.7 g of acrylic acid with the addition of 0.54 g of p-toluenesulphonic acid and 50 mg of di-tert.-butylhydroquinone and 50 mg of p-methoxyphenol in toluene.

25.0 g of this ester were reacted with 3.9 g of isocyanatoethyl methacrylate (produced by Dow Chemical) with the addition of 4 mg of Desmorapid SO (Rheinchemie Rheinau GmbH).

1 g of the polymerizable resin thus obtained was mixed with 50 mg of Irgacure 651 (Ciba-Geigy), and 2 g of phosphate buffer (pH 7, 0.01M) were added. 200 mg of alcohol dehydrogenase (from yeast, supplied by Boehringer Mannheim, containing 120 mg of enzyme protein of specific activity 400 U/mg) were dissolved in this solution, and a film 500 μm thick of this solution was formed and irradiated for 10 min. with a high pressure mercury lamp so that a solid film was produced.

One quarter of the product thus obtained (corresponding to 30 mg of alcohol dehydrogenase) was cut into small pieces which were placed in a 100 ml conical flask and 0.1M tris. HCl, pH 8.6, containing 142 mg of NAD, Li salt (supplied by Boehringer Mannheim), 0.1M semicarbazide, 5% analytical grade ethanol, were added to a final volume of 20 ml.

Samples were taken from the reaction solution at set times and, after dilution, the UV-VIS spectrum of the NADH which was being produced was measured. The total amount of NAD had been reduced to NADH after about 50 minutes, the initial rate being 8.1 μmol/min. Thus the immobilized alcohol dehydrogenase has a specific activity of 0.28 U/mg of immobilized enzyme protein. It was possible to use the immobilized product repeatedly.

Example 2

Immobilization of Alcohol Dehydrogenase 1 g of the polymerizable resin obtained in Example 1 was mixed with 50 mg of 1,2-diphenyl-2-hydroxy-3-[N-(N-methyl)pyrollidinium]-1-propanone methylsulphate, and 1.5 g phosphate buffer (0.01M, pH 7) were added. 200 mg of alcohol dehydrogenase (from yeast, supplied by Boehringer, Mannheim, containing 120 mg of enzyme protein, 400 U/mg) were dissolved in this solution, and the solution was added dropwise to 100 g of a mixture of silicone oil/paraffin oil with a specific gravity of 0.9 g/cm$^3$, beads being formed by vigorous stirring and passing through of nitrogen and these were polymerized by irradiation for 15 minutes with a high pressure Hg lamp.

1.0 g of the beads thus obtained were incubated in 50 ml conical flasks with 10 ml of 0.1M potassium phosphate, pH 8.5, 10 mM NADH, 1% acetaldehyde, on an orbital shaker at 230 rpm and 30° C.

After 6 h, about 50% of the NADH used, 50 μmol, had been oxidized to NAD, the initial rate being 0.23 μmol/min.

Example 3

Immobilization of lipase 1 g of the polymerizable resin from Example 1 was mixed with 50 mg of Irgacure 651 (Ciba-Geigy), and 3 g of phosphate buffer (0.01M, pH 7) were added. 0.8 g of lipase (from *Candida cylindracea*, Sigma) were dispersed in this solution. The entire mixture was then spread onto a polyamide fabric (Monodur PA 250 N, Verseidag-Industrietextilien GmbH) and irradiated with a high pressure mercury lamp for 10 min., so that a solid film, strengthened by the polyamide fabric, was produced.

160 mg of lipase which has undergone inclusion in the abovementioned polymer, corresponding to 72 cm$^2$ of cut foil, were incubated in 40 ml of H$_2$O with 2 g of sucrose palmitate stearate 15 (supplied by Serva, Heidelberg) at 25° C. Liberated fatty acids were titrated with 0.1N NaOH using a pH-stat (pH 7.1).

The activity of immobilized lipase was calculated to be 5.8 mU/mg of dry lipase products (1 U=1 μmol of fatty acid liberated per minute).

Example 4

Immobilization of lipase 197 g of octaethylene glycol were esterified with 36 g of acrylic acid with the addition of 2 g of p-toluenesulphonic acid and 0.35 g of di-tert.-butylhydroquinone and 0.35 of p-methoxyphenol in toluene. 100 g of the ester thus obtained were reacted with 47 g of isophorone diisocyanate and 90 mg of Desmorapid SO.

5 g of the polymerizable resin thus obtained were dissolved in 2 g of 0.01M potassium phosphate buffer, pH 7.0, mixed with 6 g of a lipase suspension (lipase from *Candida cylindracea*, supplied by Sigma; 17% solids content), and 100 mg of Irgacure 651 (Ciba-Geigy) were added. This aqueous lipase mixture was spread onto a polyamide strengthening fabric (Monodur PA 250N, Verseidag-Industrietextilien GmbH) and was polymerized by irradiation for 10 minutes with a high pressure Hg lamp.

72 cm$^2$ of the immobilized lipase thus obtained were introduced into 40 ml of water at pH 7.1, and 1.0 g of sucrose palmitate stearate 15 (supplied by Serva, Heidelberg) was added at 25° C. Liberated fatty acids were titrated with 0.1N NaOH on a pH-stat. 2.74 ml of 0.1N NaOH were consumed each hour, which corresponds to 274 μmol of free fatty acids. The liberation of fatty acids was calculated to be 0.065 μmol/min per cm$^2$ of immobilized lipase foil.

Example 5

Immobilization of esterase 25.0 g of the ester prepared in Example 1 were reacted with 2.3 g of Desmodur N (Bayer AG, Leverkusen) and 1.4 g of isophorone diisocyanate with the addition of 7.5 mg of Desmorapid SO (Rheinchemie Rheinau GmbH).

5 g of the polymerizable resin thus obtained, 250 mg of Irgacure 651 (Ciba-Geigy), 8.5 g of phosphate buffer (0.01M, pH 7) and 3 ml of esterase suspension (from pig liver, Boehringer Mannheim GmbH) were mixed and spread onto a polyamide fabric (Monodur PA 250N, Verseidag-Industrietextilien GmbH). After irradiation with a high mercury lamp, a film strengthened by the polyamide fabric was obtained.

36 cm$^2$ of the esterase foil thus obtained were incubated in 45 ml of 0.1M sodium phosphate, pH 7.0, with 5 ml of a 100 mM solution of dimethyl nitroterephthalate in methanol at 30° C. on a rotating shaker.

The reaction solution was analyz ed by HPLC. The starting compound was no longer detectable after 48 h. The two monoesters of nitroterephthalic acid and, in a small amount, nitroterephthalic acid were formed.

Example 6

Immobilization of L-lactate Dehydrogenase 5 g of the polymerizable resin used in Example 5 were mixed with 250 mg of phenylglyoxylic acid, 5 g of phosphate buffer (0.01M, pH 7) and 3 ml of L-lactate dehydrogenase suspension (from pig muscle, Boehringer Mannheim GmbH, containing 10 mg/ml of enzyme protein, specific activity about 550 U/mg), and the mixture was processed to form a film in analogy to Example 5.

Half of the film thus obtained, containing about 15 mg of enzyme protein, was cut up and incubated with 20 ml of 0.1M potassium phosphate buffer (pH 8.0), 10 mM NADH, 0.05M pyruvate Na salt, in a 100 ml conical flask. The temperature was 30° C., and the reaction solution was shaken on a shaker at 200 strokes per minute.

Samples were taken from time to time and, after dilution, the decrease in NADH was determined by photometry using a blank sample without immobilized L- lactate dehydrogenase as the reference. The total amount of NADH had been oxidized to NAD after 60 minutes. The initial rate was determined to be 3.9 μmol/min, which corresponds to a specific activity of 0.26 U/mg of enzyme protein having undergone inclusion.

Example 7

Immobilization of L-lactate Dehydrogenase 1 g of the polymerizable resin obtained in Example 5 was mixed with 50 mg of 1,2-diphenyl-2-hydroxy-3-[N(N-methyl)pyrrolidinium]-1-propanone methylsulphate, and 1.5 g of phosphate buffer (0.01M, pH 7) were added. 0.6 ml of L-lactate dehydrogenase (from pig muscle, supplied by Boehringer, Mannheim, containing 10 mg/ml of enzyme protein about 550 U/mg) was dissolved in this solution, and the solution was added dropwise to 100 g of a mixture of silicone oil/paraffin oil with a specific gravity of 0.9 g/cm$^3$, beads being formed by vigorous stirring and passing through of nitrogen, and these were polymerized by irradiation with a high pressure Hg lamp for 15 minutes.

The resulting beads were incubated with 20 ml of 0.1M potassium phosphate buffer, (pH 8.0), 10 mM NADH, 0.05M pyruvate Na salt in a 100 ml conical flask at 30° C. and 200 rpm.

Samples were removed, diluted and assayed by photometry for the decrease in NADH using a blank sample as reference.

The total amount of NADH had been oxidized to NAD after 3 h. The initial rate was 1.4 μmol/min.

Example 8

Immobilization of Baker's Yeast 100.0 g of polyethylene glycol with a mean molecular weight of 1,000 (Chemische Werke Hüls) were esterified with 7.2 g of acrylic acid with the addition of 0.92 g of p-toluenesulphonic acid and 0.1 g of di-tert.-butylhydroquinone and 0.1 g of p-methoxyphenol in toluene.

75.0 g of the ester thus obtained were reacted with 8.3 g of isophorone diisocyanate with the addition of 9 mg of Desmorapid SO.

5.0 g of the polymerizable resin were mixed with 0.1 g of Irgacure 651 (Ciba-Geigy) and 1.0 g of buffer solution (0.01M, pH 7). A mixture of 13.7 g of baker's yeast (25% solids content) and 13.7 g of buffer solution (0.01M, pH 7) was added to this solution. The mixture thus obtained was sprayed onto a polyamide fabric and irradiated with a high pressure mercury lamp so that a solid film was produced.

36 cm$^2$ of the film thus obtained were assayed for their NADH oxidase activity. For this purpose, the film was cut up, placed in a 200 ml conical flask, and 0.05M potassium phosphate buffer, pH 8.0, and 360 mg of NADH (grade I, Boehringer Mannheim), were added to a final volume of 50 ml, and the mixture was incubated on a rotating shaker at 200 rpm and at 30° C. with a blank sample without immobilized baker's yeast as reference.

The immobilized yeast cells oxidized NADH at a rate of 5.3 μmol/h, the mean measured over 48 h. This reaction can be used for the regeneration of NAD by O$_2$ in coupled enzyme systems.

Example 9

Immobilization of Baker's Yeast 218.9 g of polyethylene glycol with a mean molecular weight of 1,550 (Chemische Werke Hüls) were esterified with 9.8 g of acrylic acid with the addition of 2.3 g of p-toluenesulphonic acid, 0.23 g of di-tert.-butylhydroquinone and 0.23 g of p-methoxyphenol in toluene.

165.8 g of the ester thus obtained were reacted with 18.2 g of isocyanatoethyl methacrylate (Dow Chemical) with the addition of 36 mg of Desmorapid SO.

9.0 g of this polymerizable resin were mixed with 90 mg of Irgacure 651 and with 2.7 g of phosphate buffer (0.01M, pH 7). The solution thus obtained was added to a mixture of 20.0 g of baker's yeast and 20.0 g of phosphate buffer (0.01M, pH 7), and a film 500 μm thick was formed from this and polymerized by irradiation with a high pressure mercury lamp.

36 cm$^2$ of the foil thus obtained were assayed for NADH oxidase activity. The foil was cut up, placed in a 200 ml conical flask and 0.05M potassium phosphate buffer, pH 8.0, and 360 mg of NADH (grade I, supplied by Boehringer, Mannheim) were added to a final volume of 50 ml, and the mixture was incubated on a rotating shaker at 200 rpm at 30° C. with a blank sample of the same composition but without immobilized baker's yeast as reference. NADH was oxidized at a rate of 7.4 μmol/h, the mean measured over 48 h.

Example 10

Immobilization of Baker's Yeast 5.0 g of the polymerizable resin from Example 8 were mixed with 0.1 g of phenylglyoxylic acid and 1.0 g of buffer solution (0.01M, pH 7). A mixture of 13.7 g of baker's yeast (25% solids content) and 13.7 g of buffer solution of pH 7 was added to this solution. The mixture thus obtained was then dispersed in beads in 200 ml of a mixture of paraffin oil and silicone oil with a specific gravity of 0.9 g/cm$^3$, while stirring and passing through nitrogen, and was polymerized using a high pressure mercury lamp.

15 g of these beads were incubated with 50 ml of 0.01M potassium phosphate, pH 8.0, 1 mM NADH (grade II, supplied by Boehringer, Mannheim) in a 200 ml conical flask at 25° C. on an orbital shaker at 230 rpm.

The NADH oxidase activity of the immobilized yeast cells was determined by the decrease in the NADH content by photometry with a blank sample without yeast cells as reference.

15 g of immobilized product had an activity of 0.24 U (1 U=1 μmol of NADH oxidized per min). This reaction can be used to regenerate NAD in coupled enzyme systems.

Example 11

Immobilization of Baker's Yeast 9.0 g of the polymerizable resin from Example 9 were mixed with 90 mg of phenylglyoxylic acid, and 2.70 g of phosphate buffer (0.01M, pH 7) were added.

The solution thus obtained was added to a mixture of 20.0 g of baker's yeast and 20.0 g of phosphate buffer (0.01M, pH 7), and beads were prepared from this in analogy to Example 10.

15 g of moist beads were incubated with 50 ml of 0.01M potassium phosphate, pH 8.0, 1 mM NADH (supplied by Boehringer, Mannheim) in a 200 ml conical flask at 25° C. on an orbital shaker, 230 rpm. On the basis of the photometrical determination of NADH, 15 g of beads had an activity of 0.14 U.

Example 12

Immobilization of Baker's Yeast 4.0 g of phosphate buffer (0.01M, pH 7.0) were added to 10 g of the polymerizable resin from Example 13 so that a solution was produced. The solution thus obtained was added to a mixture of 17.5 g of baker's yeast and 17.5 g of a phosphate buffer (0.01M, pH 7.0). Then 0.2 g of ammonium peroxydisulphate was dissolved in this, and 0.2 g of N,N,N',N'-tetramethylethylenediamine was added. After thoroughly mixing in a beaker, the solution polymerized within a few minutes.

The resulting block was cut into small pieces (approximately 5×5×3 mm) and assayed for NADH oxidase activity, in analogy to Example 9. 10 g of the moist polymer were used in this assay. NADH was oxidized at a rate of 19.3 μmol/h.

A control experiment was a parallel mixture of the same composition but without immobilized baker's yeast, but no decrease in the NADH content of this was found.

Example 13

Immobilization of *Protaminobacter rubrum*

110.0 g of the ester from Example 9 were reacted with 7.4 g of isophorone diisocyanate with the addition of 15 mg of Desmorapid SO.

5.0 g of the polymerizable acrylate resin thus obtained were mixed with 50 mg of Irgacure 651, and 2.0 g of phosphate buffer (0.01M, pH 7) were added so that a solution was produced.

The strain *Protaminobacter rubrum* (CBS 574.77) was used for the production of sucrose mutase. The nutrient solution consisted of 5% syrup, 2% cornsteep liquor and 0.05% (NH$_4$)$_2$HPO$_4$, the pH is 7.2. 200 ml of nutrient solution in a 1 l conical flask innoculated with 1 ml of a *Protaminobacter rubrum* suspension. The fermentation continued for 15 h at 31° C. on an orbital shaker.

20 liters of the above nutrient solution in a liter fermenter were innoculated with this preculture and fermented at 31° C. for 16 h. The fermentation solution was concentrated by a factor of 10 by microfiltration.

17.5 g of this concentrated fermentation solution were mixed with the abovementioned acrylate resin solution and spread in a polyamide fabric (Monodur PA 250N, Verseidag-Industrietextilien GmbH). A polyamide-strengthened film was produced after irradiation with a high pressure mercury lamp for 15 minutes.

In order to assay the immobilized *Protaminobacter rubrum* cells, their sucrose mutase activity was measured. For this purpose, 36 cm$^2$ of foil were incubated in 50 ml of 50% sucrose solution, pH 7.0, at 30° C. on a rotating shaker, and samples were taken at various times. The conversion of sucrose into isomaltulose was determined by HPLC. The conversion rate was 0.60 g/h sucrose, which corresponds to 620 U/g of dry cells. 1 μmol of sucrose converted per min corresponds to 1 U.

Example 14

Immobilization of *Protaminobacter rubrum*

*Protaminobacter rubrum* (CBS 574.77) was cultured in analogy to Example 13.

6 g of phosphate buffer (0.01M, pH 7.0) were added to 20 g of the polymerizable resin from Example 9. The solution thus obtained was mixed with 180 g of Protaminobacter cell suspension which had been concentrated by a factor of about 10 by microfiltration. After 0.4 g of ammoniumperoxidisulphate had been dissolved in this solution, 0.4 g of N,N,N',N'-tetramethylethylenediamine was added, and the mixture was thoroughly mixed and poured rapidly into several dishes so that the thickness of the layer of poured material was about 3 mm. Polymerization started after a few minutes, and the polymerized discs were cut into small pieces 5×5×3 mm in size, and these were packed in a 500 ml column.

After a flow rate of about 90 ml/h had been set up, 72% of the sucrose in a 50% sucrose solution had been converted at 30° C. into isomaltulose and by-products. An increase in the flow rate to 135 ml/h led to a decrease in the conversion of sucrose to 52.7%.

Example 15

Immobilization of *Protaminobacter rubrum*

The strain *Protaminobacter rubrum* (CBS 574.77) is used for the production of sucrose mutase, and it was cultured in analogy to Example 13.

10 g of the polymerizable acrylate resin obtained in Example 9 were mixed with 3.0 g of phosphate buffer (0.01M, pH 7) and 500 mg of Irgacure (Ciba-Geigy). 70 g of a fermentation broth which contained *Protaminobacter rubrum* cells and had been concentrated by microfiltration were added to this solution, and this mixture was added dropwise to 460 g of a silicone oil having a specific gravity of 0.95 g/cm$^3$. Dispersion of the abovementioned cell-containing mixture to form beads was achieved by vigorous stirring and passing through of nitrogen, and these were polymerized with two high pressure mercury lamps irradiating for half an hour.

6.0 g of the beads thus obtained were incubated with 50 ml of 50% sucrose solution, pH 7.0, in a 200 ml conical flask on an orbital shaker at 230 rpm. The reaction solution was analyzed by HPLC. The immobilized Protaminobacter cells converted 0.32 g of sucrose per hour.

Example 16

Immobilisation of *Protaminobacter rubrum*

*Protaminobacter rubrum* (CBS 574.77) was cultured in analogy to Example 13.

110 g of the ester from Example 9 were reacted with 7.4 g of isophorone diisocyanate with the addition of 15 mg of Desmorapid SO.

10 g of the polymerizable acrylate resin thus obtained were mixed with 4 g of phosphate buffer 0.01M, pH 7.0, and 500 mg of 1,2-diphenyl-2-hydroxy-3-[N(N-methyl)- pyrrolidium]- 1-propanone methylsulphate and 35 g of concentrated fermentation broth, and the mixture was added to 300 g of a silicone oil/paraffin oil mixture with a specific gravity of 0.9 g/cm$^3$, and beads were prepared in analogy to Example 15.

6.0 g of the beads thus obtained were tested with 50% sucrose solution in analogy to Example 15. The immobilized Protaminobacter cells converted 0.69 g of sucrose per hour.

Example 17

Immobilization of *Protaminobacter rubrum*

*Protaminobacter rubrum* (CBS 574.77) was cultured in analogy to Example 13.

10 g of the polymerizable resin from Example 16 were mixed with 4 g of phosphate buffer (0.01M, pH 7.0) and 35 g of concentrated fermentation broth, and 0.3 g of ammonium peroxidisulphate was dissolved in. This mixture was added dropwise to 2,000 g of a silicone oil of density 0.97 g/cm$^3$, in which 0.3 g of N,N,N',N'-tetramethylethylenediamine was dissolved, with vigorous stirring, so that the aqueous mixture was dispersed to form beads and polymerized within a short time.

The entire mass of beads was packed into a column of length 25 cm and diameter 2 cm, the adherent silicone oil was displaced by 50% sucrose solution, and the column was operated continuously at 45° C. At a flow rate of 28 ml/h, 54.5% of the 50% sucrose solution was converted into isomaltulose and by-products.

Example 18

Drying and Reuse of Immobilized Preparations

The beads obtained in Examples 16 and 17 were dried overnight by passing dehydrated air of a temperature between 30° and 35° C. over the beads which results in shrinking and in an increase of hardness.

After 4 weeks of storage at room temperature the dried beads of Example 16 or 17 were rehydrated and assayed according to Example 16 or 17 showing 87% or 84%, respectively, of their original activity.

It will be understood that the specification and examples are illustrative but not limitative of the present invention and that other embodiments within the spirit and scope of the invention will suggest themselves to those skilled in the art.

What is claimed is:

1. In the immobilization of biological material by polymerizing a polymerizable compound in the presence of biological material, the improvement which comprises employing as the polymerizable compound an aqueous solution of a polymerizable compound which is readily soluble in water, contains two or more polymerizable functional groups per molecule and has a molecular weight of over 400 wherein said polymerizable compound is selected from the group consisting of a polyethyerpolyol in which some of the hydroxyl groups have been esterified with acrylic and/or methacrylic acid and the remainder have been reacted with an isocyanate group-containing derivative of an unsaturated carboxylic acid and a polyetherpolyol in which some of the hydroxyl groups have been esterified with acrylic acid and/or methacrylic acid and the remainder have been reacted with a polyfunctional isocyanate.

2. A process according to claim 1, wherein in the improvement the aqueous solution contains the biological material and is dispersed in a second, inert liquid medium to form beads, and this aqueous phase in the form of beads is polymerized.

3. A process according to claim 2, wherein in the improvement the inert liquid medium comprises a water-immiscible medium selected from the group consisting of aliphatic, cycloaliphatic or aromatic hydrocarbons.

4. A process according to claim 2, wherein in the improvement polymerization is carried out to produce beads of mean diameter 0.05 mm to 5 mm.

5. A process according to claim 2, wherein in the improvement the ratio of the weight of the aqueous phase to that of the inert liquid medium is between 1:1 and 1:20.

6. A process according to claim 2, wherein in the improvement the dispersion of the aqueous phase to form beads is brought about by stirring and/or by passing through inert gas or by spraying the aqueous phase into the inert liquid medium.

7. A process according to claim 1, wherein in the improvement a radical polymerization initiator and/or a radical polymerization initiator redox system and/or an accelerator is present during polymerization.

8. A process according to claim 7, wherein in the improvement a water-soluble radical polymerization initiator is used which comprises ammonium peroxydisulphate, and wherein a water-soluble accelerator is used which comprises N,N,N',N'-tetramethylethylenediamine.

9. A process according to claim 1, wherein in the improvement a photoinitiator is added, and polymerization is carried out by irradiation.

10. A process according to claim 9, wherein in the improvement polymerization is carried out by irradiation with actinic light with the addition of a photosensitizer which is poorly soluble in the inert liquid medium.

11. A process according to claim 1, wherein in the improvement an aqueous solution or dispersion of the biological material is mixed with polymerizable compound or an aqueous solution thereof in a weight ratio between 1:1 and 30:1.

12. A process according to claim 1, wherein
  (a) the polyether-polyol is a polyethylene glycol with a molecular weight of 400 and above, and
  (b) the polyfunctional isocyanate comprises a member selected from the group consisting of isophorone diisocyanate, toluylene diisocyanate, hexamethylene diisocyanate, polyisocyanate containing biuret groups and a polyisocyanate which has been produced from the reaction of a diisocyanate with a polyhydric alcohol.

13. A process according to claim 1, wherein in the improvement the biological material comprises a fermentation broth.

14. A process according to claim 13, wherein the fermentation broth is pre-concentrated.

15. A process according to claim 2, wherein in the improvement the inert liquid medium comprises a water immiscible medium selected from the group consisting of silicone oils and paraffin oils.

16. A process according to claim 2, wherein in the improvement the beads are dried and the entrapped biological material remains fully active.

17. The product produced by the process of claim 1.

18. In the immobilization of biological material by polymerizing a polymerizable compound in the presence of the biological material, the improvement which comprises employing as the polymerizable compound an aqueous solution of a polymerizable compound which is readily soluble in water, contains two or more polymerizable functional groups per molecule and has a molecular weight of over 400 wherein said polymerizable compound is a polyethylene glycol with a molecular weight of 400 and above in which some of the hydroxyl groups have been esterified with acrylic and/or methacrylic acid and the remainder have been reacted with an isocyanate group-containing derivative of an unsaturated carboxylic acid the isocyanate group-containing derivative comprises a member selected form the group consisting of isocyanatoethyl acrylate, isocyanatoethyl methacrylate and 4-isocyanato-3-methyl-2-butyl-acrylate.

19. In the carrying out of biotransformations by contacting a substrate with a immobilized biological material, the improvement which comprises using an immobilized biological material obtained by polymerizing a polymerizable compound in the presence of the biological material wherein said polymerizable compound is selected from the group consisting of a polyetherpolyol in which come of the hydroxyl groups have been esterified with acrylic and/or methacrylic acid and the remainder have been reacted with an isocyanate group-containing derivative of an unsaturated carboxylic acid and a polyetherpolyol in which some of the hydroxyl groups have been esterified with acrylic acid and/or methacrylic acid and the remainder have been reacted with a polyfunctional isocyanate.

* * * * *

UNITED STATES PATENT AND TRADEMARK OFFICE
CERTIFICATE OF CORRECTION

PATENT NO. : 4,774,178

DATED : Sep. 27, 1988

INVENTOR(S) : Egerer et al.

It is certified that error appears in the above-identified patent and that said Letters Patent is hereby corrected as shown below:

| | |
|---|---|
| Title Page, under "U.S. Patent Documents", line 6 | Correct spelling of --Lantero-- |
| Col. 1, line 5 | Correct spelling of --invention-- |
| Col. 1, line 41 | Correct spelling of --with-- |
| Col. 2, line 41 | Correct spelling of --in-- |
| Col. 5, line 30 | Correct spelling of --linkage-- |
| Col. 8, lines 36 - 40 | Italicize --Aspergillus ... Clostridia-- |
| Col. 8, line 43 | Do not italicize --Examples-- |
| Col. 9, line 65 | Correct spelling of --Immobilization-- |
| Col. 13, line 47 | Insert --30-- after "a" |

Signed and Sealed this

Eighth Day of August, 1989

Attest:

DONALD J. QUIGG

*Attesting Officer*      *Commissioner of Patents and Trademarks*